United States Patent
Zamfes (10) Patent No.: US 6,715,347 B2
(45) Date of Patent: Apr. 6, 2004

(54) APPARATUS AND METHOD FOR DETERMINING MEASURES OF THE PERMEABILITY OF HC-BEARING FORMATIONS USING FLUORESCENCE

(76) Inventor: Konstandinos S. Zamfes, 1830-10th Avenue S.W., Calgary, Alberta (CA), T3C 0J8

( * ) Notice: Subject to any disclaimer, the term of this patent is extended or adjusted under 35 U.S.C. 154(b) by 191 days.

(21) Appl. No.: 10/073,915

(22) Filed: Mar. 28, 2002

(65) Prior Publication Data

US 2004/0016289 A1 Jan. 29, 2004

Related U.S. Application Data

(63) Continuation-in-part of application No. 09/568,855, filed on May 11, 2000, now abandoned.

(51) Int. Cl.[7] .......................... E21B 49/00; G01N 15/08; G01V 5/00; G01T 1/167
(52) U.S. Cl. .................... 73/152.05; 73/38; 250/255; 250/301
(58) Field of Search .................... 73/38, 152.05; 250/301, 302, 253, 255, 458.1, 461.1, 459.1

(56) References Cited

U.S. PATENT DOCUMENTS

| | | | |
|---|---|---|---|
| 2,297,939 A | * 10/1942 | Campbell | 250/255 |
| 2,361,261 A | * 10/1944 | Campbell | 250/255 |
| 2,435,843 A | * 2/1948 | Rand | 250/255 |
| 2,459,512 A | * 1/1949 | Fash et al. | 250/301 |
| 2,490,642 A | * 12/1949 | Lipson | 250/301 |
| 4,797,906 A | * 1/1989 | Smith | 250/255 |
| 4,977,319 A | * 12/1990 | Supernaw | 250/255 |
| 4,990,773 A | * 2/1991 | Supernaw et al. | 250/255 |
| 5,012,674 A | * 5/1991 | Millheim et al. | 73/152.05 |
| 5,049,738 A | * 9/1991 | Gergely et al. | 250/301 |
| 5,237,539 A | * 8/1993 | Selman | 367/69 |
| 5,269,999 A | * 12/1993 | Smesny | 264/570 |
| 5,686,724 A | * 11/1997 | Spilker et al. | 250/255 |
| 5,789,662 A | * 8/1998 | Dayal | 73/38 |

* cited by examiner

Primary Examiner—Michael Cygan
(74) Attorney, Agent, or Firm—Sean W. Goodwin (57) ABSTRACT

Formation drilling cuttings are centrifuged and a sediment sample is extracted and heated to burn off surface hydrocarbons. A non-fluorescing diluant is added to the sediment. The sediment is then subjected to UV excitation. Depending upon the permeability of the sediment, the speed at which emitted fluorescence brightens is found to vary. The time and brightness of the emission are measured. The time/brightness relationship is proportional to the permeability of the cuttings and can be used to calculate a relative permeability index for comparison to other know parameters to determine the presence of hydrocarbon and the likelihood of being able to produce the hydrocarbon from a wellbore.

23 Claims, 10 Drawing Sheets

APPARATUS AND METHOD FOR DETERMINING MEASURES OF THE PERMEABILITY OF HC-BEARING FORMATIONS USING FLUORESCENCE

CROSS REFERENCE TO RELATED APPLICATION

This application is a continuation-in-part of U.S. patent application Ser. No. 09/568,855 filed on May 11, 2000, now abandoned, the entirety of which is incorporated herein by reference.

FIELD OF THE INVENTION

The invention relates to methods for determining the permeability of hydrocarbon-bearing formations through the measurement of fluorescence from formation samples.

BACKGROUND OF THE INVENTION

The permeability of material, such as rock found in hydrocarbon formations, is a very desirable piece of information to geologists and drilling engineers. While all soils and rock are permeable, the degree of permeability is highly variable. The measurements of permeability of a soil or rock indicate how well a fluid will flow through the pores of the material.

It has been known for some time to measure the permeability of core samples and drilling mud removed from hydrocarbon-bearing formations.

U.S. Pat. No. 4,253,327 to Phillips Petroleum Company in 1981 describes the use of elevated pressure and temperature to determine the permeability of a core sample. A core sample is heated and a fluid is supplied under a first desired pressure and allowed to flow through the sample. A second pressure is applied to the surface area of the sample and the pressure measured of the fluid flowing to the first and second face of the sample. The permeability is calculated based on the pressure differential across the core sample.

U.S. Pat. No. 5,133,207 to Wilson et al. describes a complex system of instrumentation designed to measure the permeability of multiple core samples in which a fluid under pressure is provided along with a plurality of permeameters each having an inlet and an outlet and a means for measuring the amount of fluid passing through the core sample in each permeameter.

The above techniques require elaborate sample preparation and are typically performed off the drilling site. Further, Applicant is unaware of any permeability tests for cuttings samples from returned drilling mud.

It would be advantageous to have a method of determining permeability of a hydrocarbon-bearing formation that minimizes sample preparation and can be performed on site, thereby providing realtime permeability information to the drilling engineer.

Fluorescence techniques are also known, which are simply to shine a broad spectrum ultraviolet light on a sample of cuttings, fluorescence being a crude indicator of the presence of oil. Techniques are also known for testing drilling mud samples for the presence of hydrocarbons using these fluorescent techniques.

U.S. Pat. No. 2,361,261, to Campbell describes a method of determining whether an oil producing zone has been penetrated by comparing fluorescence from drilling fluids samples discharge from the well to that entering the well. The samples are subjected to UV light and the fluorescence measured using conventional instrumentation which provides a reading on a galvanometer which can be converted into terms of oil by comparing to samples of standard drilling fluid with known amounts of oil added. Campbell teaches separating out and removing the coarse particles. A small amount of solvent may be added to the sample however, it is not added to extract oil from the main body of the sample, but merely to concentrate surface oil. Campbell does not contemplate utilizing the methodology to provide information regarding sample porosity and permeability.

U.S. Pat. No. 2,435,843 to Rand describes a method for examining well cuttings for the presence of hydrocarbons. A sample of cuttings is placed in a shallow dish containing sufficient non-fluorescing solvent to cover the sample which is then exposed to an ultraviolet light. An observer visually examines the same for release of plumes of fluorescence released from the sample. Rand's method does not teach continued immersion of the sample in the solvent, but instead requires an immediate examination when the sample is placed in the solvent. Rand's method relies upon qualitative observation and subjective comparison on the part of the observer to provide data regarding time a vigor of plume formation to determine porosity and permeability of samples. While Rand suggests that logs can be made of the color, number and vigor of the plumes observed from samples taken at various depths to be used as a useful adjunct to logs of other types, he does not teach any means of quantitative measurement, nor does he teach a method of standardizing observations between samples to provide standardized comparative data.

Another such technique is described in U.S. Pat. No. 4,990,773 to Supernaw et al. which involves testing for hydrocarbon producability by determining the amount of highly viscous asphaltenes present in drilling mud samples. A sample solvated in a polar solvent which solvates asphaltenes is compared to a sample solvated in an aliphatic solvent which solvates most crude fractions without solvating the asphaltenes. The solvates are exposed to UV light at approximately 254 nm at which wavelength most petroleum compounds fluoresce. The amount of fluorescence emitted is measured at 320 nm and a ratio between the two samples is used to determine the producability of the hydrocarbon formation.

Further, in U.S. Pat. No. 4,977,319 to Supernaw describes a similar technique used to determine the hydrocarbon content of an underground formation. The sample is simply solvated with a solvent which readily solvates hydrocarbons. The solvate is quantitatively measured using a fluorometer with an excitation wavelength below 400 nm. Most petroleum compounds fluoresce at this excitation wavelength. The results are compared to previous data obtained comparing intensity against a predetermined correlation of fluorescence and oil fraction. As disclosed, Supernaw and the prior art identified therein teach the measurement of fluorescence intensity at one or more wavelengths.

The current invention builds on the known techniques of solvation of hydrocarbons and measurement of emitted fluorescence to expand the known measurement techniques to now include determination of permeability of drilling mud samples.

SUMMARY OF THE INVENTION

A method is provided for testing drilling mud and establishing a measure of the permeability of the cuttings contained therein.

In a preferred embodiment, cuttings sediment is centrifuged from drilling mud, heated to drive off surface hydrocarbons and is subjected to light for fluorescence excitation. A non-fluorescent diluant is added to the sediment and the fluorescence emission is measured. Dependent upon the permeability of the sediment, the speed at which the fluorescence brightness develops is found to vary. Specifically, both the time and brightness of the emission are monitored. The time/brightness relationship is proportional to the permeability of the cuttings. While the brightness and the permeability can be estimated by the experiment eye, it is preferable and more reliable to use apparatus capable of providing reproducible, standardized fluorescence measurement. Preferably, a blank is used to calibrate the background brightness of the diluant alone or a detect a diluant which has been contaminated.

Having determined brightness measurements over time, a fluorescence index can be calculated and used, along with other known parameters such as grain size, angularity, sortability and a porosity factor, to calculate a permeability index.

In a broad aspect, a method of semi-quantitatively identifying the presence of hydrocarbons filling the pores of cuttings samples from a drilled formation is performed, the hydrocarbons being fluorescence when exposed to UV light, and comprising the steps of;
  adding a non-fluorescent diluant to the sample;
  exciting the sample;
  measuring elapsed time;
  measuring the intensity of the fluorescence emission as a function of the elapsed time for establishing a relationship for that sample; and
  establishing a numerical value for a representative brightness of the fluorescence emission as a function of the elapsed time (FI).

Accordingly, in another aspect of the invention, a method is provided for quantifying a fluorescence index (QFI) for a sample from a drilled formation comprising the steps of:
  assigning a numerical value to the percentage of a sample that fluoresces when excited for establishing a quantity factor QTY; and
  determining a quantitative fluorescence index for the sample being substantially proportional to QTY and FI.

Accordingly, in another aspect of the invention, a method is provided for quantifying a permeability index (PI) for a sample from a drilled formation comprising the steps of:
  assigning numerical values for the proportion grains in each of a plurality of grain size divisions within a sample and a weighting factor for each division corresponding thereto for establishing a environmental index value EnviroNdx;
  assigning a numerical value to the degree of angularity of grains within a sample for establishing an angularity index value AngNdx;
  assigning a numerical value to the degree to which the grains within a sample are the same for establishing a sorting index value SrtNdx;
  assigning a numerical value to the degree of porosity of the sample for establishing a porosity value Por; and
  determining the relative index PI of the sample as being substantially proportional to QFI EnvNdx, AngNdx, SrtNdx, and Por.

Most preferably the relationship is as follows:

$$PI = QFI \times EnvNdx \times AngNdx \times SrtNdx \times Por$$

DETAILED DESCRIPTION OF THE PREFERRED EMBODIMENT

Figure 1:
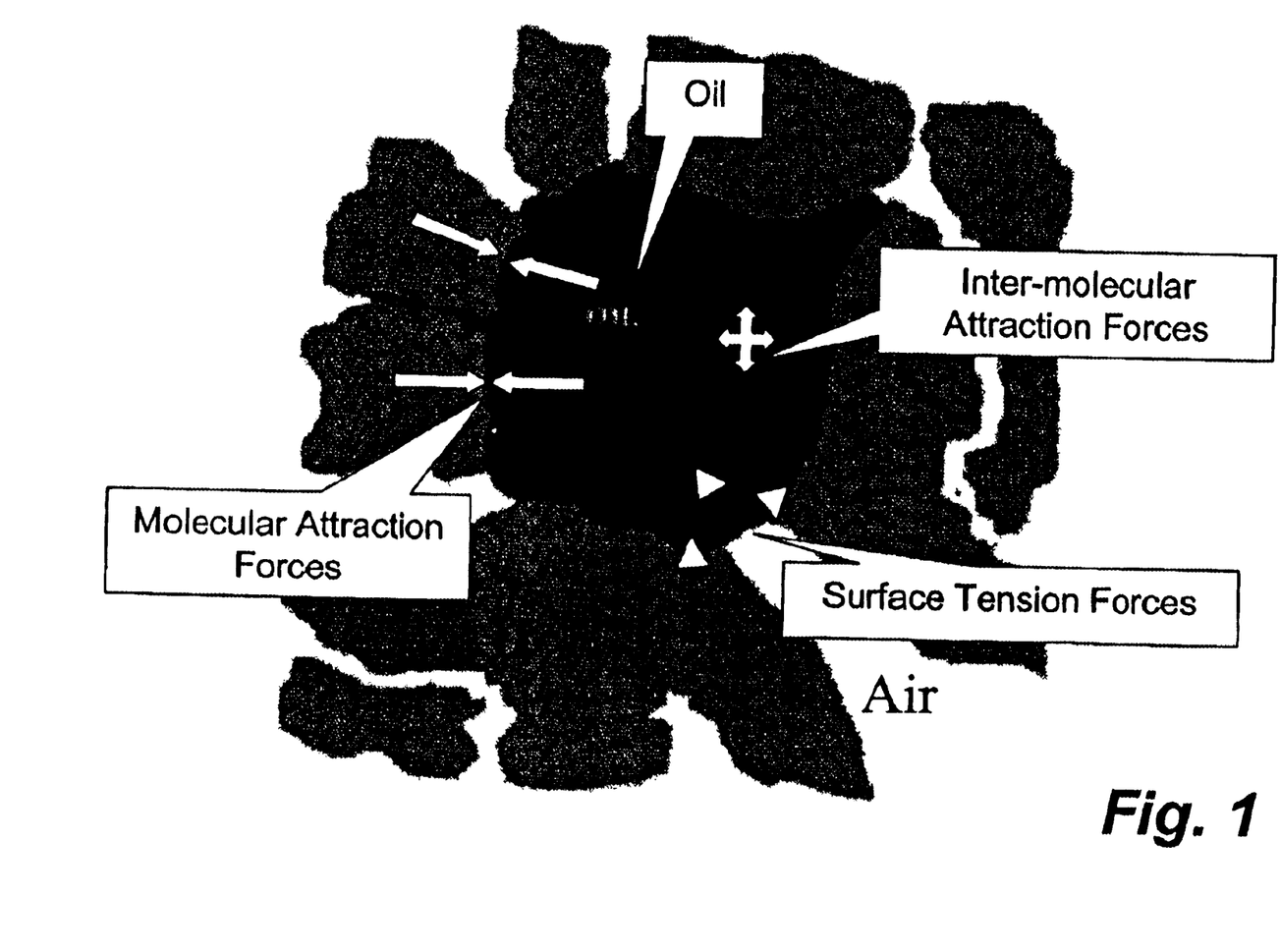
FIG. 1 is a fanciful schematic illustrating the relationship between a cuttings sample and hydrocarbon trapped within the sample's pores.

Having reference to FIG. 1, a diagrammatic model illustrates forces which act on liquid hydrocarbons HC or oil present within the very tiny pores of a porous structure found within a formation. These forces determine to what degree the liquid hydrocarbons trapped therein are recoverable. Very simplistically, molecular attraction forces MF act at the surface of the liquid Hc and at the surface of the sample essentially gluing the Hc to the sample rendering it unrecoverable. Surface Tension ST forces act against the sides of the small pores. Intermolecular forces and intermolecular attraction are the forces resulting from the viscosity of the liquid Hc. The complex interaction of all of these forces and the degree to which they are present contribute to how permeable the formation is. Typically, samples of cuttings from the formation are removed during drilling and tested to determine that relative permeability. Based on the results, a geologist can determine whether it is likely an acceptable volume of gas or liquid Hc can be produced from the formation. Usually analysis is done contemporaneous with the well drilling program; however, sometimes the samples are stored for a protracted period of time. It has been determined that, as a result of the strong forces acting upon the hydrocarbon which retain it within the pores, samples can be maintained for years and retested as required such as when new interest is generated for an old well.

To evaluate a formation, a sample of cuttings are obtained either from, the drilling mud generated during drilling, or from previous samples saved from older drilling programs. In the case of a current drilling program, a sample of drilling mud is centrifuged and the sediment, representing cuttings from a subterranean formation, is heated on a hot plate at approximately 800° C., until the surface of the sample has reached at least 400° C. and at least a portion of the surface hydrocarbons have been burned off. Removal of at least a portion of the surface hydrocarbon increases the selectivity of the test towards the pore hydrocarbons. The sediment sample is then placed in a first sample tray. A second sample tray, without sample, is used as a blank.

Figure 2:
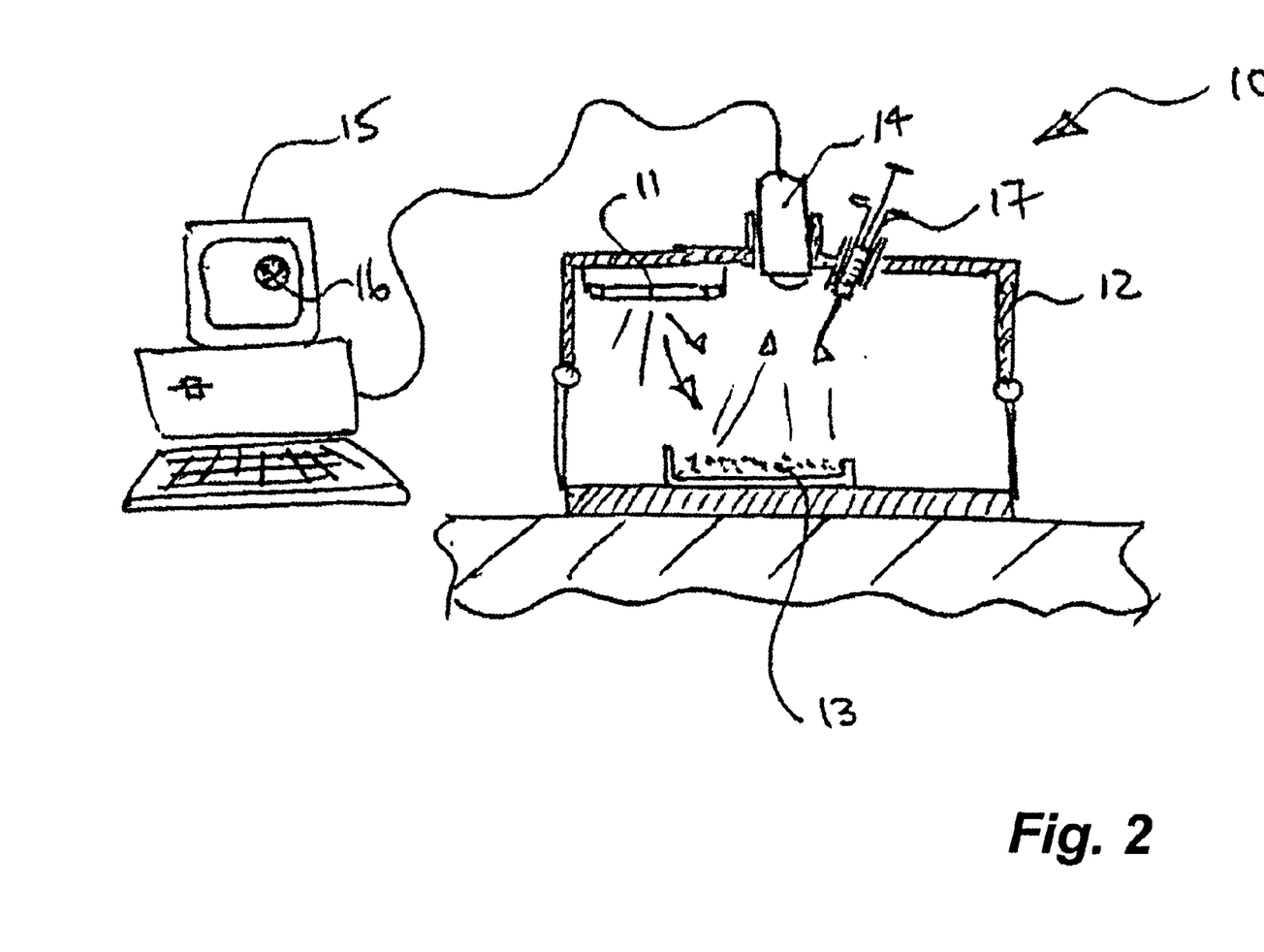
FIG. 2 illustrates a diagrammatic representation of fluorescence testing equipment of one embodiment of the invention.

Referring to FIG. 2, in one embodiment of the invention a fluorescent apparatus 10 is provided which comprises a light 11 in a light-proof enclosure or cabinet 12 into which samples 13 are passed. The apparatus 10 further comprises a fluorescent emissions sensor 14, including devices such as a photomultiplier tube (PMT), charge-coupled device (CCD) or a digital camera, communicating with a microcomputer 15. A stop watch, timer or microprocessor timer 16 is employed.

A diluant injector 17 applies a drop of diluant solvent such as lighter fluid or ID Orange (tradename), a 1,1,1-Trichloroethane substitute to the sediment sample 13.

To determine sediment characteristics, It is preferable to first add diluant to the blank, which is then stimulated or excited with light, preferably with a blue UV light, and is observed to confirm no fluorescence is being emitted. Toluol has also been used as a diluant solvent but its use is restricted now due to its carcinogenic characteristics. This initial calibration step confirms that the non-fluorescent diluent used in the process has not been contaminated with any fluorescing compounds Then a drop of the solvent is added to the sediment and a timer (stop watch, or electronic timer) is started for measuring elapsed time.

The sediment is exposed to the same blue UV light as used for the blank. Brightness readings resulting from fluorescent emissions are measured by eye or using a quantitative fluorometer and are recorded at timed intervals.

Surprisingly, the speed at which the brightness increases has been observed by the inventor to be proportional with the permeability of the sediment sample, and therefore, the permeability of the formation which had been drilled. As is the case with the prior art techniques, the brightness reached is proportional to the oil content.

It is hypothesized that, as the solvent permeates the samples, the hydrocarbons are solvated, overcoming the internal forces, reducing the surface tension and thus being more easily released from the sediment pores so as to be able to be excited by the excitation wavelength. The greater the permeability, a greater quantity of solvent permeates the sediment, and at a faster rate; exciting more hydrocarbon and causing an increase in brightness.

Figure 3:
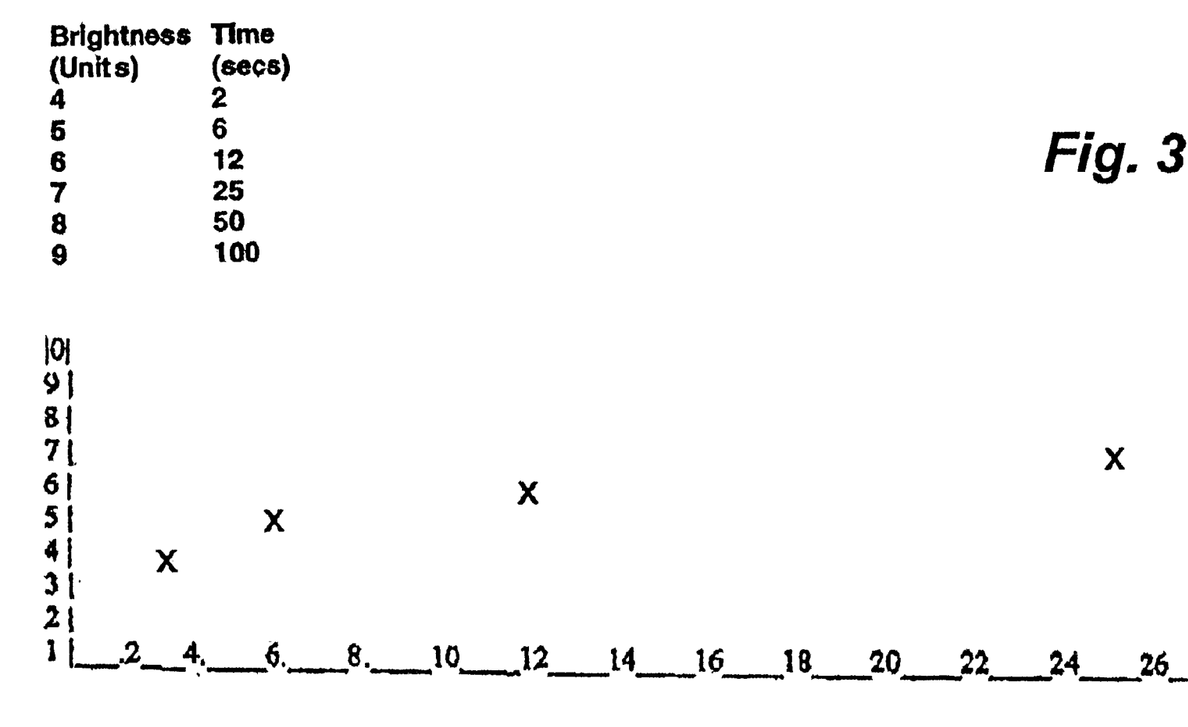
FIG. 3 is a graph demonstrating sample fluorescence brightness over time

Having reference to FIG. 3, using a relative and a dimensionless brightness scale, each emission brightness is correlated against elapsed time. As shown, a sediment sample which rises to a brightness of 6 in 12 seconds is much more permeable than is a sample which required 25 seconds to reach a brightness of 7. The saturation brightness is different for different concentrations of hydrocarbon in the sediment. A rule of thumb is that saturation in 3 seconds is pipelineable, 5 seconds is excellent, 8 seconds is good and thereafter is fair to poor.

The brightness can be compared to brightness data from drilling mud of different permeability to determine the degree of permeability of the sample.

Factors which can affect the results include: the formation permeability, the concentration of hydrocarbons in the sample pores and conversely the water saturation, the pore pressure (which affects the release of hydrocarbons from the pores). Clearly however, regardless of the water saturation, if there is a fast and bright response, then there is good permeability and hydrocarbons present.

Figure 4:
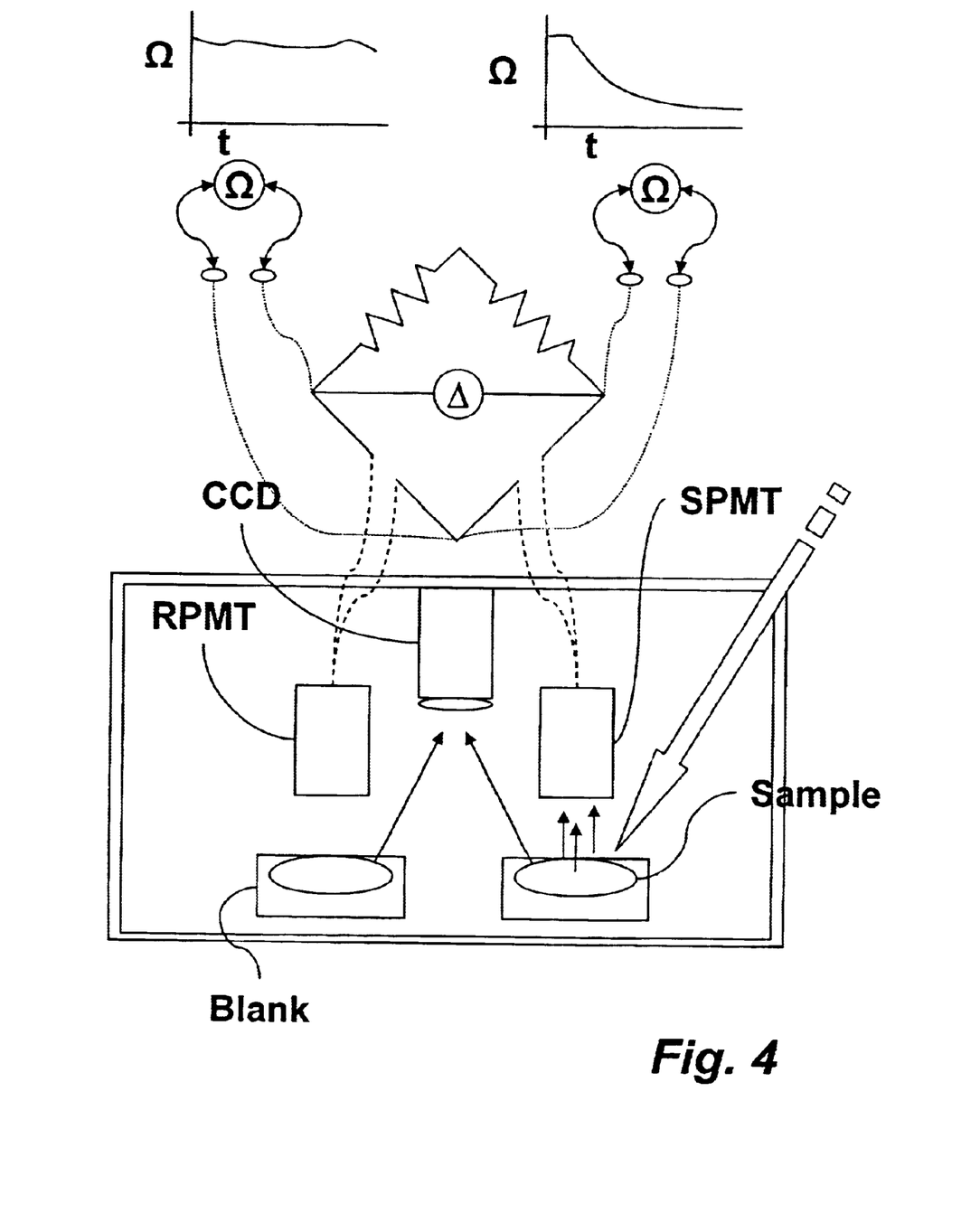
FIG. 4 is a schematic of an alternate embodiment of fluorescence testing equipment illustrating PMT measurement equipment for a blank and a sample.

Having reference to FIG. 4, and in another embodiment of the invention, apparatus 100 is provided which comprises a reference photon counter or photomultiplier tube (RPMT) 101 and a sample photomultiplier tube 102 (SPMT). Each PMT 101, 102 is positioned over a shallow dish, the RPMT 101 over a blank dish 103 and the SPMT 102 over a dish 104 containing a cuttings sample 105. The RPMT and SPMT 101, 102 are connected through a Wheatstone bridge 106. Both dishes 103, 104 are subjected to blue UV light as in the first embodiment. A drop of solvent is added to the sample 105 in the sample dish 104. As the sample 105 begins to fluoresce, photons 107 reach the SPMT 102 and the resistance begins to drop. The greater the number of photons 107 reaching the SPMT 102, the brighter the fluorescence and the larger the drop in resistance. The resistance is measured at predetermined intervals until there is substantially no further decrease and the inverse is plotted as a function of time as being representative of brightness (Bri).

The RPMT can be used to correct for any fluorescence which may be present as a result of environment contamination, background or noise in the PMT's.

A visual assessment of the sample is made at maximum fluorescence to determine the percentage of the total surface area of the sample that is fluorescing. The value is expressed as a percentage of the total and provides a quantity factor (QTY) to be used in further assessment of the data.

In a preferred embodiment of the invention, a digital camera 14, as shown in FIG. 2, replaces the PMT's shown in FIG. 4 and is positioned over the sample dishes. Brightness data is collected by the cameras light sensitive sensor array or charge-coupled device (CCD) in a video sequence. Software used to analyze the data is capable of selecting identical areas from each sequence. Bit depth, as digital data, is obtained for each pixel in the selected area for each sequence or at predetermined intervals throughout the sequences, the produce a similar brightness-versus-time plot as is obtained by the PMT response. Further, the images may provide a relatively simple means by which the percent of total surface area fluorescing can be estimated at a later time.

The maximum brightness of the sample, the observation of fluorescence produced over time and the shape of the curve, representing rate of fluorescence emission, can provide information regarding the porosity and permeability of the sample. Additionally, the information can also be used in conjunction with other known parameters to calculate even more particular semi-quantitative values of relative permeability (PI). Applicant has previously disclosed such parameters, relating to angularity (AngNdx), sortability (SrtNdx), porosity (Por) and grain size (EnvNdx), in issued U.S. Pat. No. 6,301,953 to Applicant, the details and entirety of which are incorporated herein by reference.

Further, Applicant has disclosed the calculation of other indices to which the fluorescence can be compared, Hydrocarbon saturation index (HcSI,) to indicate the fraction of hydrocarbon in the pores of a porous sample, and Hydrocarbon Ratio (HcR), to determine the nature of the hydrocarbon present, both of which are described in issued U.S. Pat. No. 6,290,000 to Applicant, the details and entirety of which are incorporated herein by reference.

Fluorescence Index (QFI)

Figure 5A:
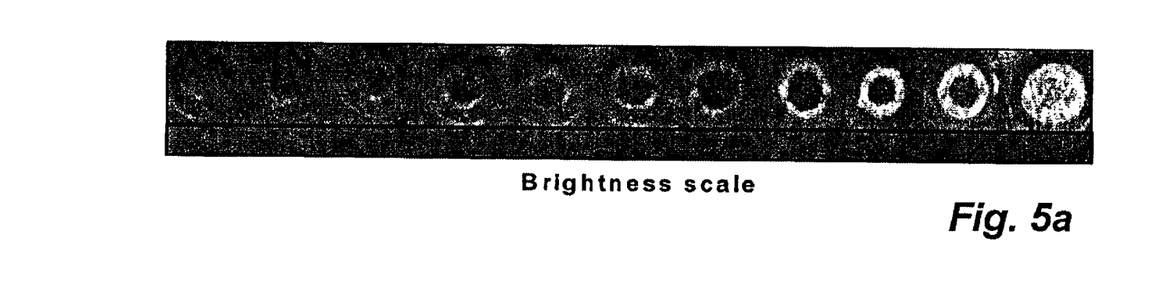
FIG. 5a illustrate a series of digital snapshots of samples which illustrate increasing brightness over time.
Figure 5B:
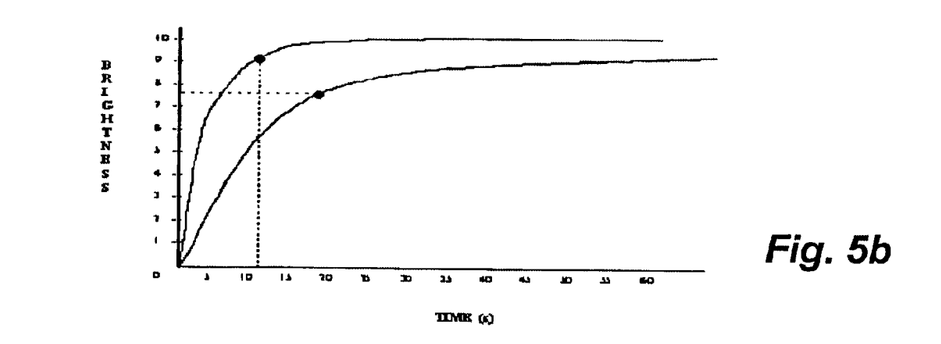
FIG. 5b is a graph illustrating increasing fluorescence brightness over time for two different samples and selection of the time to 90% of saturation.
Figure 5C:
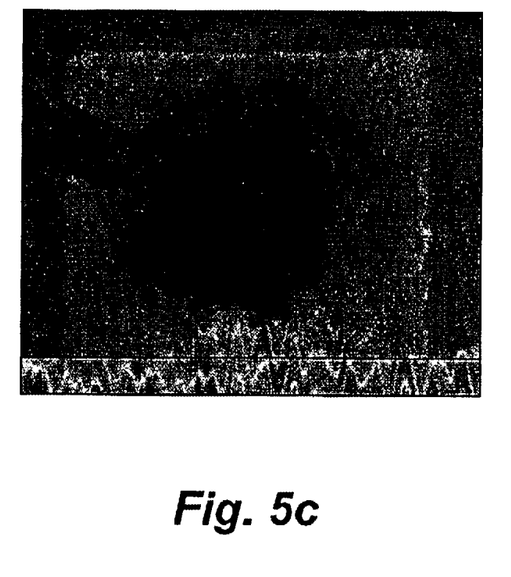
FIGS. 5c and 5d illustrate the contrast between a non-fluorescing and a fluorescing sample.
Figure 5D:
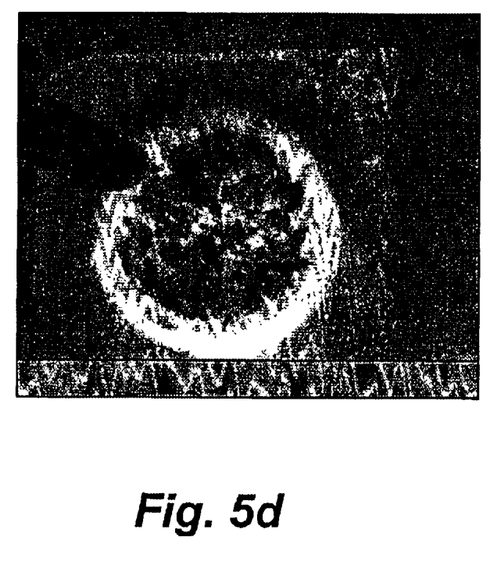

With reference to FIGS. 5a and 5b, a fluorescence index is calculated from the brightness (Bri) versus time (t) plot to provide a numerical value indicative of the amount of hydrocarbon present in each sample. As shown in FIG. 5a, there is a clear increase in the overall brightness of the fluorescence of a sample. Referring then to FIG. 5b, complete saturation B (100%) is reached when there is no longer a measurably significant increase in fluorescence over time. Empirically, it has been determined there is sufficient sensitivity remaining in the curve, even from test to test, where a representative brightness value (RBri) is read from the curve at about 90% of complete saturation (B) and is divided by time (t) to provide a fluorescence rate or index (FI). All other variables being assumed constant, two curves C1 and C2 are illustrated, one demonstrating a high permeability where at 90% of saturation B (at about 10 units) is reached in about 12 seconds and another sample (reaching saturation B at about 9.2 units) having lower permeability where 90% of saturation B is reached in about 18 seconds.

$$FI = \frac{RBrl}{t} \text{ or } \frac{\sim 90\%B}{t}$$

Quantitative Fluorescence Index (QFI)

Further, a quantitative fluorescence index (QFI) can be determined as being directly proportional to the fluorescence index (FI) and the percentage of grains fluorescing of the total grains, or surface area.

$$QFI=FI \times QTY$$

Grain size (EnvNdx)

As described in applicant's patent U.S. Pat. No. 6,301,953, analytical techniques have long been known for assessing populations in a sample and such techniques can be used to place quite accurate percentages of the fraction of size in the sample. Thus, if a sample is assessed of graded as having 20% Fine (grain grade of 2) and 80% Coarse grains (grain grade of 8 for a total of 10), with none of the other grades present, an index (the "Environmental Index" or "EnvNdx" for short) can be calculated by multiplying the assessed percentage for each grain by its corresponding weighting factor and then summing the totals as follows:

|  | V | F | M | C | VC |  |  |
|---|---|---|---|---|---|---|---|
| Grain grade | 0 | 2 | 0 | 8 | 0 |  |  |
| Weighting | 1 | 2 | 3 | 4 | 5 |  |  |
| Environmental Index | 0 | 4 | 0 | 32 | 0 | = | 36 |

Conversely, if a sample has 80% Fine (grain grade of 8) and 20% Coarse grains (grain grade of 2), without any of the other grades present, the resulting Environmental Index is determined as follows:

|  | V | F | M | C | VC |  |  |
|---|---|---|---|---|---|---|---|
| Grain grade | 0 | 8 | 0 | 2 | 0 |  |  |
| Weighting | 1 | 2 | 3 | 4 | 5 |  |  |
| Environmental Index | 0 | 16 | 0 | 8 | 0 | = | 24 |

The above examples illustrate a numerical and semi-quantitative indication of permeability of the sample, having an EnvNdx of 36 being deemed more permeable that one having an EnvNdx of 24.

Angularity Index (AngNdx)

The shape of grains within sedimentary rock is also indicative of its permeability. Angularity of grains within the sample is conventionally rated according to categories outlined in Table 2.

TABLE 2

| Rate | Abbrev. | Description |
|---|---|---|
| Angular | A | sharp and pronounced protrusions |
| Subangular | a | many protrusions somewhat rounded |
| Subrounded | r | rounded, less pronounced protrusions |
| Rounded | R | rounded |

For the purposes of calculation of relative permeability, the categories above are assigned numerical values of 1 through 4 for rating A, a, r and R, respectively. Thus, the more angular a sample, the less permeable it is likely to be and conversely, the less angular, the more permeable.

Sorting Index (SrtNdx)

A sorting rating based on the number of different grain sizes present within the sample is conventionally rated according to categories outlined in Table 3.

TABLE 3

| Rate | Abbrev | Number of size grades |
|---|---|---|
| Well | W | 1 or 2 size grades |
| Medium | M | 3 or 4 size grades |
| Poor | P | 5 or more size grades |

For the purpose of calculation of relative permeability, the categories above are assigned numerical values of 3,2 and 1 W, M and P respectively. Thus, having fewer size grades within a sample is indicative of greater permeability than having a plurality of varying sizes within a sample.

Porosity

Porosity is generally graded on a scale of 0–20%, however for the purposes of quantification, this scale has been expanded to 0–40%. The expansion of the scale, wherein the previously graded to 20% is now graded to 40%, allows for a greater distinction between samples and provides a greater spread of values when used to calculate a permeability index.

Permeability Index (PI)

Permeability has most commonly been assessed by the wellsite geologist based, in part, on a subjective compilation of the aforementioned physical characteristics of cutting samples.

It has been found that combining the indexes in a novel calculation, where permeability is proportional to the quantitative fluorescence index (QFI), the environmental index, the angularity index and solids sorting and porosity, a relative permeability index can be calculated.

The permeability index is therefore calculated by the following formula, $$PI=QFI \times EnvNdx \times AngNdx \times SrtNdx \times Por$$

where:
PI=permeability index
QFI=Quantitative Fluorescence Index
EnvNdx=environmental index
AngNdx=angularity index
SrtNdx=sorting index
Por=% porosity

EXAMPLE 1

Figure 6:
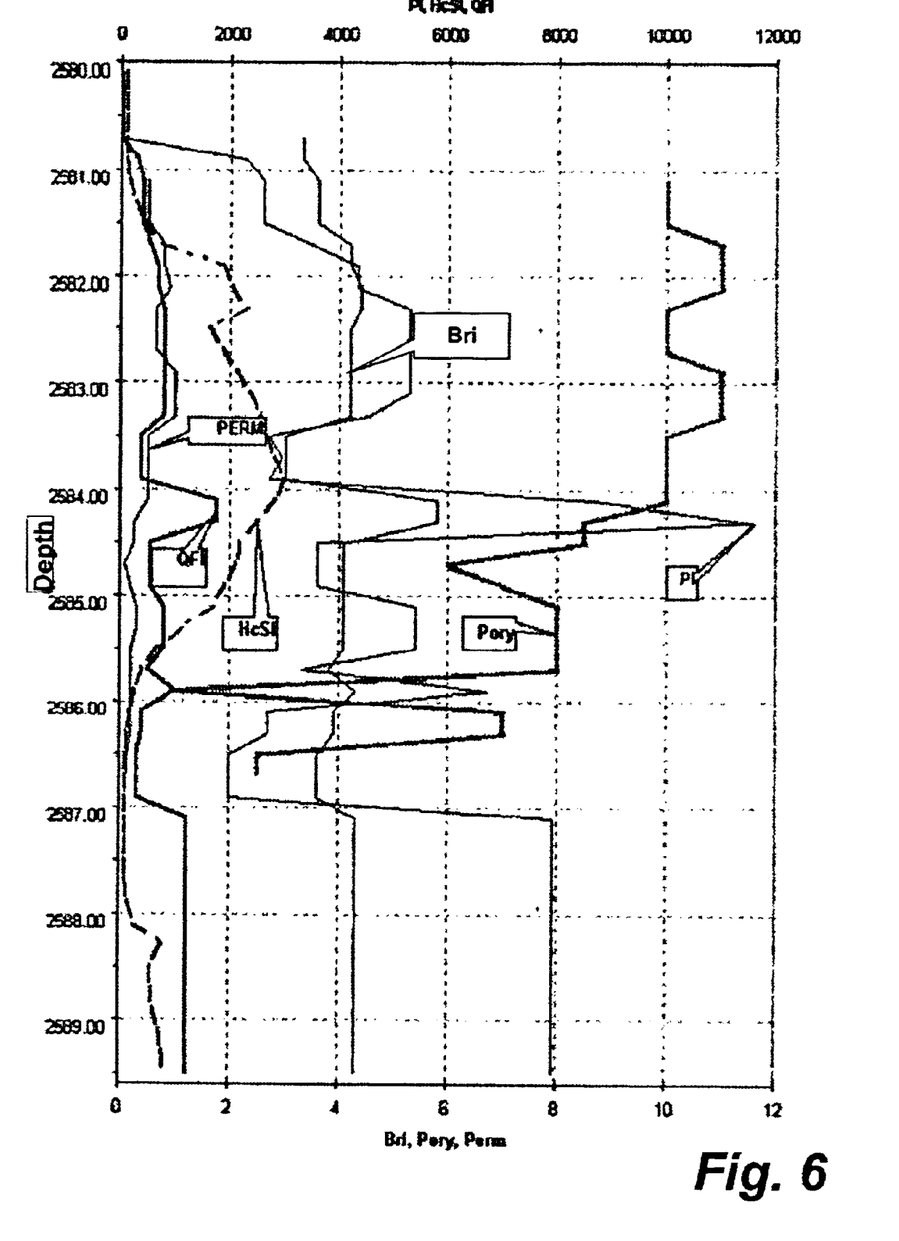
FIG. 6 is a graphical representation of various relationships between the limitations of conventional porosity (Pory) and conventional measures of permeability (PERM) conducted on core samples from a formation as they compare with and measures of relative permeability index (PI) calculated from an embodiment of the fluorescence methodology which is then related to other calculated indices.

FIG. 6 is a chart representing parameters measured or calculated from old core samples from a well. The conventional parameters of permeability (PERM) reading at a maximum of about 1 mdarcy and porosity (Pory) at 11.5% would typically indicate that the well would not produce sufficient hydrocarbon to warrant drilling. It is highly probably that this well would eventually have been plugged and abandoned.

According to the first embodiment, and referring to the curve Bri alone, there is already strong indication between 2584 and 2584.5 m that there is an enhanced permeability, contrary to the conventional PERM and Pory indicators.

Further, by applying measured brightness (Bri) with other formation factors to calculate PI, the signal to noise ratio is significantly improved to demonstrate an even stronger permeability correlation at a depth between 2583.50 m and 2584.50 m. The strong PI peak identified a zone of high permeability for recovery of any hydrocarbons. A strong hydrocarbon saturation index HcSI, corresponding to the strong PI peak (high permeability), was indicative of the presence of a high fraction of hydrocarbons in the pore space. By locating a region or zone having both a high PI and a high HcSI, there was an expectation of a flow of hydrocarbons, if completed. Further, as the Hydrocarbon Ratio HcR was also high, there was an expectation of gas. Subsequent performance and fracturing at this depth resulted in production of natural gas at a commercial rate of 5 million ft$^3$/day.

EXAMPLE 2

Figure 7:
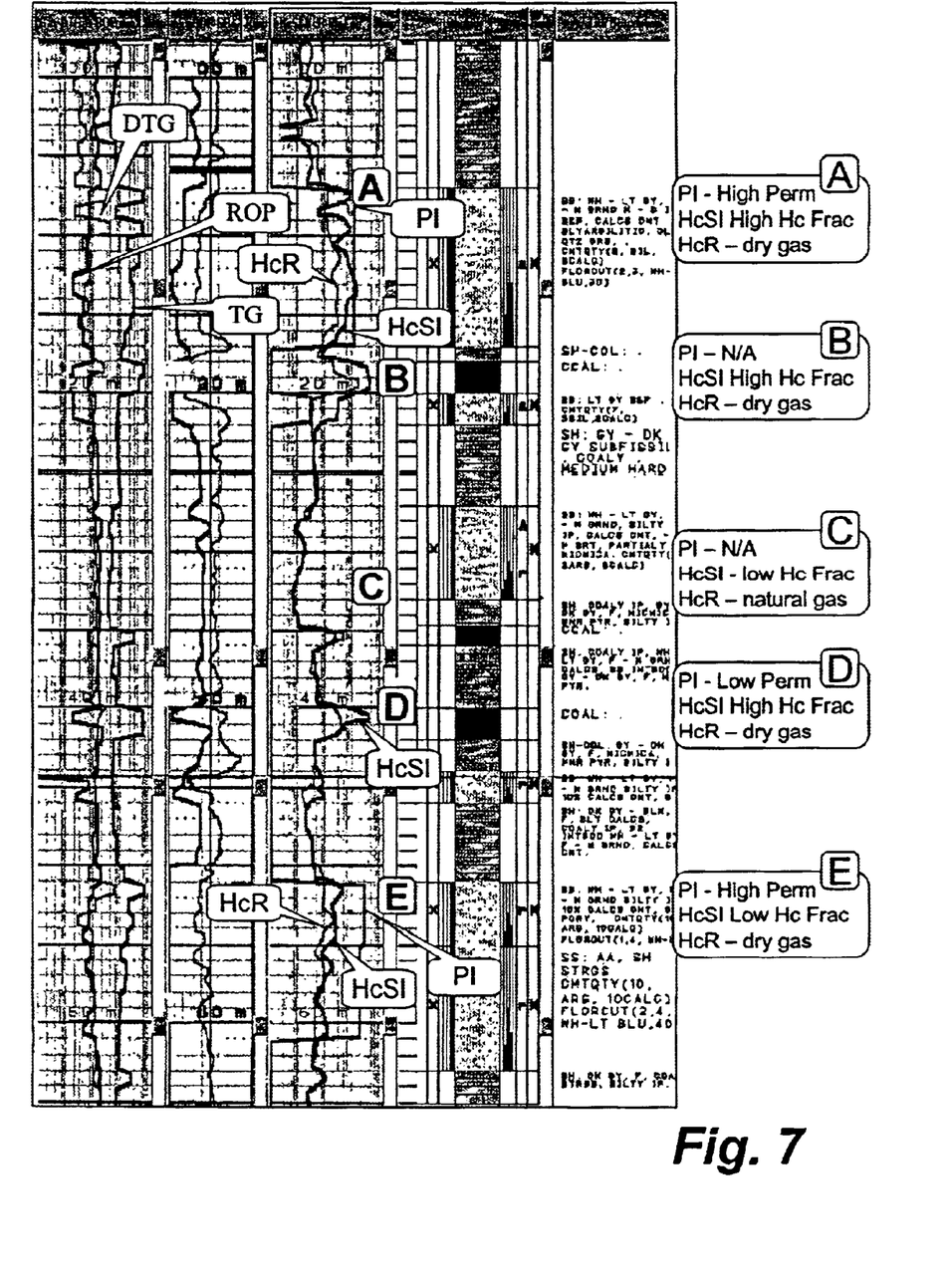
FIG. 7 is a graph of well logs which incorporate an implementation of the present invention for determining permeability index from fluorescence data and other calculated parameters of porosity and permeability.
Figure 8:
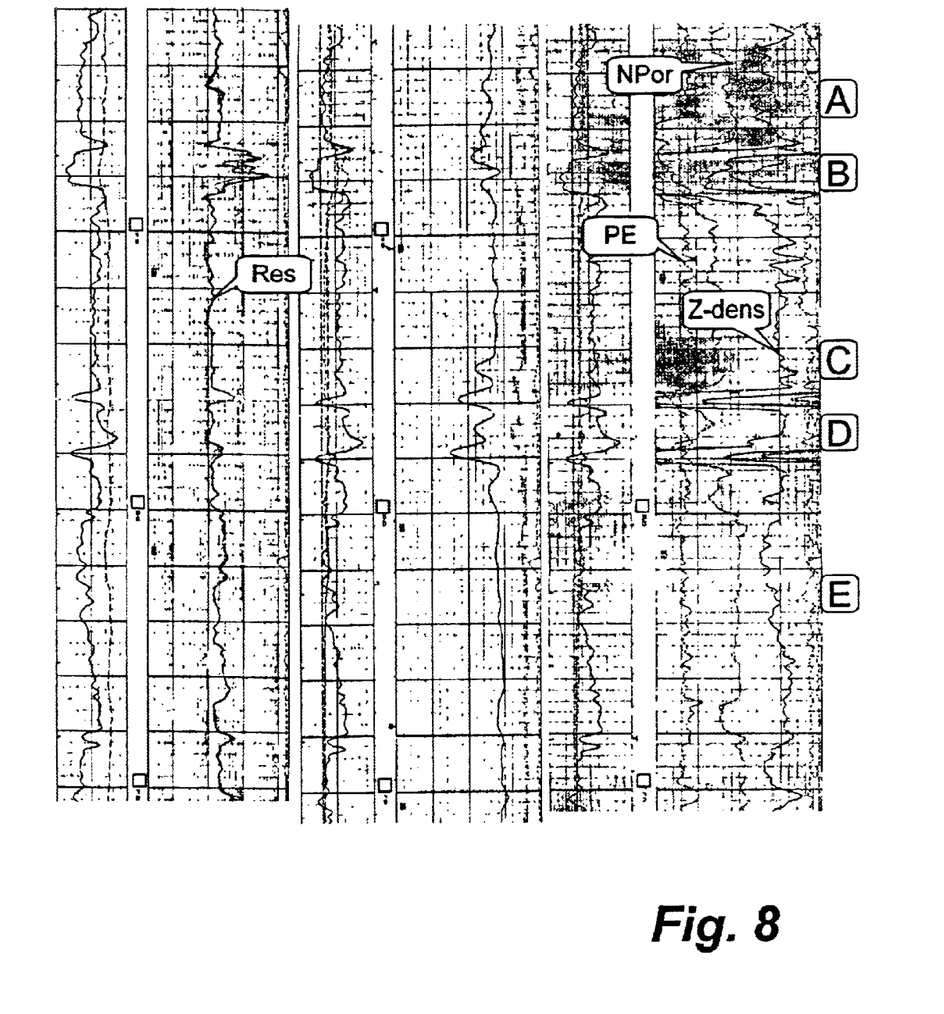
FIG. 8 is a graph of conventional well logs which correspond to the fluorescence data and other calculated parameters of porosity and permeability according to FIG. 7.
Figure 9:
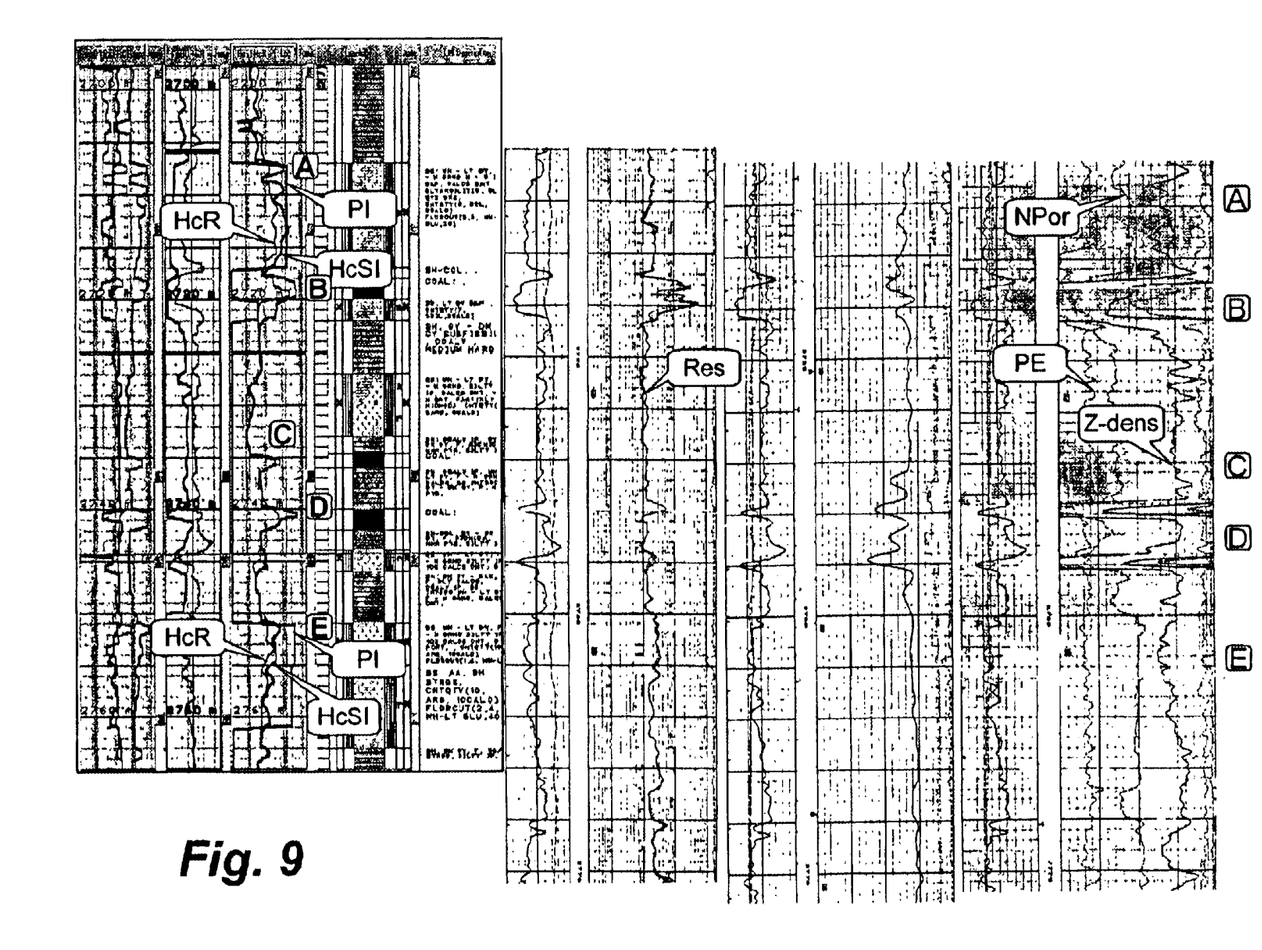
FIG. 9 is a combined graph which compares the relative permeability index calculated using fluorescence data according to FIG. 7 against the conventional well logs according to FIG. 8.

FIGS. 7–9 illustrate a comparison (FIG. 9) between PI, HcSI and HcR (FIG. 7) to convention well logs (FIG. 8) utilizing Z-density, nuclear and photoelectric effect measurements. Again, while PI is related to permeability and HcSI of the presence of hydrocarbons, HcR is related to the type of hydrocarbons.

With reference to the conventional factors including gamma ray (GR) and Resistivity (Res) represented in FIG. 8, typically a crossover of the readings for the further measurements of nuclear porosity and bulk density porosity measurements (Z-den) and photoelectric effect (PE) are supportive of the presence of recoverable hydrocarbons. Specifically, in FIG. 8, throughout the 60 of so meters of formation identified as regions A–E, there are only occurrences of crossover of the readings at regions B and D which happen to be indicative of coal bed methane and not to recoverable hydrocarbons. Based on conventional measurements, the well would have been plugged and abandoned.

A comparison of HcSI, HcR to PI, is shown in FIG. 9. Strong peak values for PI are found in regions A and E. Lower values of PI, dropping to zero, are found in regions B, C and D.

At region A, PI was high and permeability is thus determined to be high. Corresponding values for HcSI and HcR in region A were also high indicating high fractions of light hydrocarbons. Subsequent casing, perforation and fracturing of region A resulted in production of dry gas, typically methanes, at a rate of 2 m ft$^3$/day.

At region E, PI was high and permeability is thus determined to be high. Corresponding values for HcSI and HcR in region E were both lower, the HcSI indicating low fractions of hydrocarbons and the HcR being indicative of dry methane gas.

Turning to the two HcSI peaks at regions B and D, the values are consistent with coal beds, which produce methane gas. Clearly the HcSI is correspondingly high with high HcR indicative of light Hc dry gas. Permeability PI however is virtually non existent, therefore there was no point in completing either region B or D.

All measurements in region C, including the conventional well logs, are consistent with a low permeability, non-hydrocarbon producing lithology or with a lithology producing heavier hydrocarbon gas such as natural gas.

The interpretation, including magnitude of each of PI, HcSI and HcR are best left to experienced geological interpreters.

What is claimed is:

1. A method for determining the permeability of a hydrocarbon-bearing formation from a formation sample comprising the steps of:

adding a non-fluorescent diluant to the sample;

exciting the sample with light;

measuring the relationship of the brightness of the fluorescence emission from the sample as a function of elapsed time;

selecting a brightness value and a time which elapsed to reach the selected brightness value, the selected brightness value being at a brightness less than saturation; and determining a fluorescence index (FI) indicative of the sample's permeability as a ratio of the selected brightness value and the selected time.

2. The method of claim 1 further comprising the step of comparing the Fluorescence Index FI against predetermined brightness and time relationships for establishing measures of the sample's permeability.

3. The method of claim 1 further comprising the step of determining the brightness fluorescence emission of the diluant for obtaining a background fluorescence brightness which is subtracted from the brightness of the fluorescence emission.

4. The method of claim 1 further comprising the step of centrifuging drilling mud and extracting the sediment as representing the sample.

5. The method of claim 4 further comprising the step of heating the extracted sediment to a temperature sufficient to burn off at least a portion of any surface hydrocarbons.

6. The method of claim 5 wherein the temperature sufficient to burn off surface hydrocarbons is substantially between 400 and 800 degrees Celsius.

7. The method of claim 1 further comprising the step of measuring fluorescence using a photon detector and determining values indicative of the brightness.

8. The method as described in claim 1 further comprising the steps of:

selecting a representative brightness value from the fluorescence emission relationship at a predetermined fraction of the saturation brightness;

determining the representative elapsed time corresponding to the representative brightness value; and determining a ratio of the selected representative brightness value (RBri) to the selected time (t) for establishing the fluorescence index FI which is representative of the sample's permeability.

9. The method of claim 8 wherein the predetermined fraction of the saturation brightness at which the representative brightness value is selected is substantially 90 percent of saturation brightness B.

10. The method of claim 8 further comprising the step of assigning a numerical value to the percentage of the total sample which fluoresces, for establishing a quantity factor QTY.

11. The method as described in claim 10 wherein a quantitative fluorescence index (QFI) is established using the relationship:

$$QFI = FI \times QTY$$

where FI is the fluorescence index, and
QTY is the numerical value for the percentage of the total sample which fluoresces.

12. The method as described in claim 11 wherein a permeability index (PI) of the formation is determined further comprising the steps of:
assigning numerical values for the proportion grains in each of a plurality of grain size divisions within a sample and a weighting factor for each division corresponding thereto for establishing a environmental index value EnviroNdx;
assigning a numerical value to the degree of angularity of grains within a sample for establishing an angularity index value AngNdx;
assigning a numerical value to the degree to which the grains within a sample are the same for establishing a sorting index value SrtNdx;
assigning a numerical value to the degree of porosity of the sample for establishing a porosity value Por; and
determining the relative permeability index PI of the sample as being substantially proportional to QFI, EnvNdx, AngNd, SrtNdx and Por.

13. The method as described in claim 12 wherein a hydrocarbon producing zone is located comprising the steps of:
determining values for the permeability index PI for establishing the permeability of one or more zones in the formation;
determining values for a hydrocarbon saturation index HcSI corresponding to the one or more zones in the formation for establishing the fraction of the hydrocarbons therein; and
establishing the location of the producing zone where both the PI and HcSI have values which are elevated.

14. The method as described in claim 13 wherein hydrocarbon gas is located in the formation comprising the steps of:
determining values of the hydrocarbon ratio HcR corresponding to the one or more zones in the formation for establishing the quality of the hydrocarbons therein; and
establishing the location of a gas producing zone where all of the PI, HcSI, and HcR have values which are elevated.

15. The method as described in claim 13 wherein hydrocarbon liquid is located in the formation comprising the steps of:
determining values of the hydrocarbon ratio HcR corresponding to the one or more zones in the formation for establishing the quality of the hydrocarbons therein; and
establishing the location of a gas producing zone where both of the PI, and HcSI have values which are elevated and where the HcR has a value which is low.

16. Apparatus for determining a permeability index for a hydrocarbon-bearing formation from a formation sample comprising:
a light-proof enclosure having a exciting light source located therein, a sample container for holding the formation sample, and means for introducing non-fluorescing diluent to the sample container;
a timer for measuring elapsed time;
a photon counter located in the enclosure and directed at the sample container and emitting signals indicative of brightness; and
means for determining a brightness and a time at which the sample's fluorescence brightness becomes substantially saturated, the ratio of the brightness to the time being proportional to the sample's permeability index.

17. The apparatus of claim 16 wherein the exciting light source is an ultraviolet light source.

18. The apparatus of claim 16 wherein the sample photon counter comprises a photomultiplier tube.

19. The apparatus of claim 16 wherein the sample photon counter comprises a charge-coupled device.

20. The apparatus of claim 16 further comprising:
a blank container located in the housing; and
a photon counter for receiving emissions from the blank container and emitting signals indicative of enclosure background brightness so that changes in the sample's brightness are corrected for changes in the background brightness.

21. The apparatus of claim 20 wherein the exciting light source is an ultraviolet light source.

22. The apparatus of claim 20 wherein the sample photon counter comprises a photomultiplier tube.

23. The apparatus of claim 20 wherein the sample photon counter comprises a charge-coupled device.

* * * * *